(12) United States Patent
Nzike et al.

(10) Patent No.: US 9,393,368 B2
(45) Date of Patent: Jul. 19, 2016

(54) DRIVE MECHANISM FOR A DRUG DELIVERY DEVICE AND DRUG DELIVERY DEVICE

(75) Inventors: Philippe Nzike, Frankfurt am Main (DE); Steffen Raab, Frankfurt am Main (DE); Uwe Dasbach, Frankfurt am Main (DE); Uwe Boeser, Frankfurt am Main (DE); Ulrich Brüggemann, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 495 days.

(21) Appl. No.: 13/883,393

(22) PCT Filed: Nov. 11, 2011

(86) PCT No.: PCT/EP2011/069962
§ 371 (c)(1),
(2), (4) Date: May 3, 2013

(87) PCT Pub. No.: WO2012/062911
PCT Pub. Date: May 18, 2012

(65) Prior Publication Data
US 2013/0226091 A1    Aug. 29, 2013

(30) Foreign Application Priority Data
Nov. 12, 2010    (EP) .................................... 10190940

(51) Int. Cl.
*A61M 5/315*    (2006.01)

(52) U.S. Cl.
CPC ....... *A61M 5/31585* (2013.01); *A61M 5/31511* (2013.01); *A61M 5/31515* (2013.01);
(Continued)

(58) Field of Classification Search
CPC ..................... A61M 5/31583; A61M 5/31585; A61M 5/31586; A61M 5/31575; A61M 5/31571; A61M 5/31565; A61M 5/31528; A61M 5/31533; A61M 5/31525; A61M 5/3159; A61M 5/31511; A61M 5/31515
See application file for complete search history.

(56) References Cited

U.S. PATENT DOCUMENTS 4,865,591 A * 9/1989 Sams ................ A61M 5/31553
                                                             222/287
5,383,865 A * 1/1995 Michel ............. A61M 5/31556
                                                             604/186

(Continued)

FOREIGN PATENT DOCUMENTS

DE    10237258 B4    9/2006
EP    0615762        9/1994

(Continued)

OTHER PUBLICATIONS

International Search Report for Int. App. No. PCT/EP2011/069962, completed Mar. 2, 2012.

*Primary Examiner* — Bhisma Mehta
*Assistant Examiner* — Jenna Zhang
(74) *Attorney, Agent, or Firm* — McDonnell Boehnen Hulbert & Berghoff LLP (57) ABSTRACT

The drive mechanism comprises a piston rod, a dose member with a thread engaging a corresponding thread of the body to allow a helical movement of the dose member with respect to the body, a drive sleeve rotationally coupled to the dose member, and stop means provided to restrict or inhibit a movement of the drive sleeve in the proximal direction and in the distal direction with respect to the body, the drive sleeve and the piston rod being unidirectionally coupled.

14 Claims, 4 Drawing Sheets

(52) U.S. Cl.
CPC ....... *A61M5/31525* (2013.01); *A61M 5/31533* (2013.01); *A61M 5/31583* (2013.01); *A61M 5/31528* (2013.01); *A61M 5/31565* (2013.01); *A61M 5/31571* (2013.01)

(56) References Cited

U.S. PATENT DOCUMENTS

| | | | | |
|---|---|---|---|---|
| 5,626,566 | A * | 5/1997 | Petersen | A61M 5/31551 222/309 |
| 6,004,297 | A * | 12/1999 | Steenfeldt-Jensen | A61M 5/31551 604/207 |
| 2004/0210199 | A1* | 10/2004 | Atterbury | A61M 5/31566 604/224 |
| 2005/0004529 | A1* | 1/2005 | Veasey | A61M 5/31585 604/209 |
| 2006/0276753 | A1* | 12/2006 | Kronestedt | A61M 5/20 604/186 |
| 2008/0243087 | A1* | 10/2008 | Enggaard | A61M 5/31553 604/208 |
| 2009/0254047 | A1* | 10/2009 | Thogersen | A61M 5/31585 604/211 |
| 2010/0114025 | A1* | 5/2010 | Moller | A61M 5/20 604/135 |
| 2012/0143146 | A1* | 6/2012 | Strehl | A61M 5/31541 604/208 |

FOREIGN PATENT DOCUMENTS

| | | |
|---|---|---|
| EP | 1728529 | 12/2006 |
| WO | 2006/084876 | 8/2006 |
| WO | 2007/017052 | 2/2007 |

* cited by examiner

DRIVE MECHANISM FOR A DRUG DELIVERY DEVICE AND DRUG DELIVERY DEVICE

CROSS REFERENCE TO RELATED APPLICATIONS

The present application is a U.S. National Phase Application pursuant to 35 U.S.C. §371 of International Application No. PCT/EP2011/069962 filed Nov. 11, 2011, which claims priority to European Patent Application No. 10190940.6 filed Nov. 12, 2010. The entire disclosure contents of these applications are herewith incorporated by reference into the present application.

FIELD OF DISCLOSURE

The present invention relates to a drive mechanism for a drug delivery device and a drug delivery device incorporating such a drive mechanism.

BACKGROUND

Portable drug delivery devices are used for the administration of a drug that is suitable for self-administration by a patient. A drug delivery device is especially useful in the shape of a pen, which can be handled easily and kept everywhere available. A type of drug delivery device is constructed to be refillable and reusable many times. A drug is delivered by means of a drive mechanism, which may also serve to set the dose or amount to be delivered.

DE 102 37 258 B4 describes a drug delivery device in the shape of an injection pen having a drive mechanism, which allows to deliver a plurality of different prescribed doses. The drive mechanism comprises elements which are rotated relatively to one another around a common axis. They are coupled by unidirectional gears.

SUMMARY

It is an object of the present invention to disclose a new drive mechanism for a drug delivery device that allows to set a dose.

This object is achieved by a drive mechanism according to claim 1. Further objects are achieved by variants and embodiments according to the dependent claims.

The drive mechanism for a drug delivery device comprises a body having a proximal end and a distal end, a piston rod arranged within the body along an axis of rotation, a dose member having a thread, and a drive sleeve. The thread of the dose member engages a corresponding thread of the body to allow a helical movement of the dose member with respect to the body. The helical movement comprises a rotation around the axis and a simultaneous shift along the axis. The drive sleeve is arranged within the body, rotatable with respect to the body around the axis and rotationally coupled to the dose member. Stop means are provided to restrict or inhibit a movement of the drive sleeve in the proximal direction and in the distal direction with respect to the body. The drive sleeve and the piston rod are unidirectionally coupled with respect to a rotation around the axis.

The body can be any housing or any component that forms part of a housing, for example. The body can also be some kind of an insert connected with an exterior housing. The body may be designed to enable the safe, correct, and/or easy handling of the device and/or to protect it from harmful liquids, dust or dirt. The body can be unitary or a multipart component of tubular or non-tubular shape. The body may house a cartridge, from which doses of a drug can be dispensed. The body can especially have the shape of an injection pen. The term "distal end" refers to a part of the body or housing which is intended to be arranged at a portion of the drug delivery device from which a drug is dispensed. The term "proximal end" refers to a part of the body or housing which is remote from the distal end.

The term "piston rod" encompasses any element that is provided to transfer a movement to a piston, especially for the purpose of dispensing a drug. The piston rod may be flexible or not. It may be of unitary or multipart construction, and may especially be a simple rod, a lead-screw, a rack-and-pinion, a worm gear system, or the like.

In an embodiment of the drive mechanism, the dose member has a cylindrical shape and partially surrounds the drive sleeve.

In an embodiment of the drive mechanism, the stop means are provided by webs or interfaces of the body.

Embodiments of the drive mechanism may further comprise a stop member, which is arranged within the body and is rotationally locked to the body with respect to the axis, and a drive member, which is arranged within the body, is rotationally locked to the piston rod and is held in contact with the stop member. A first gear locks the drive member rotationally to the stop member in a first sense of rotation with respect to the body, and a second gear locks the drive member rotationally to the drive sleeve when the drive sleeve is rotated in a second sense of rotation, which is opposite to the first sense of rotation, with respect to the body.

In a further embodiment of the drive mechanism, the drive sleeve is rotationally locked to the dose member.

Further embodiments may comprise a clutch sleeve arranged between the dose member and the drive sleeve. The clutch sleeve forms a clutch, which couples the clutch sleeve rotationally with the dose member in a releasable manner, the clutch sleeve being rotationally locked to the drive sleeve.

In a further embodiment, the clutch locks the clutch sleeve unidirectionally rotationally to the dose member. The unidirectional rotational locking can be provided to generate a rotation of the clutch sleeve during a helical movement of the dose member with respect to the body in the proximal direction.

A further embodiment further comprises a resilient element acting on the clutch sleeve and the dose member. The resilient element, which may be a spring, for example, tends to make the clutch engage. The resilient element is arranged in such a manner that moving the dose member in the distal direction reduces or removes the engagement of the clutch.

In further embodiments the dose member can be moved helically in the distal direction without rotating the clutch sleeve.

In further embodiments the thread of the dose member is arranged in such a manner that the helical movement of the dose manner with respect to the body comprises a rotation having the first sense of rotation when the dose sleeve is moved towards the proximal end and a rotation having the second sense of rotation when the dose sleeve is moved towards the distal end.

In further embodiments the piston rod has a thread guiding the piston rod in the body in such a manner that the piston rod advances towards the distal end when the piston rod is rotated in the second sense of rotation with respect to the body.

In embodiments of the drive mechanism, a set operation may be performed by a helical movement of the dose member with respect to the body in the proximal direction, the helical movement being guided by the thread of the dose member. A dispense operation may be performed by a helical movement of the dose member with respect to the body in the distal direction, the helical movement being guided by the thread of the dose member, and the drive sleeve rotating simultaneously.

In further embodiments of the drive mechanism, a correcting set operation is performed by a helical movement of the dose member with respect to the body in the distal direction, the helical movement being guided by the thread of the dose member, and the drive sleeve being stationary with respect to the body.

The invention further relates to a drug delivery device with a drive mechanism according to one of the embodiments. The drug delivery device can especially have a body in the shape of an injection pen.

The drug delivery device can be a disposable or re-usable device designed to dispense a dose of a drug, especially a liquid, which may be insulin, a growth hormone, a heparin, or an analogue and/or a derivative thereof, for example. The device can be configured to dispense fixed doses of the drug or variable doses. The drug may be administered by a needle, or the device may be needle-free. The device may be further designed to monitor physiological properties like blood glucose levels, for example.

These and other features of the invention will become apparent from the following brief description of the drawings, detailed description and appended claims and drawings.

BRIEF DESCRIPTION OF THE FIGURES

Similar or corresponding elements of different embodiments bear the same reference numerals in the figures.

DETAILED DESCRIPTION

Figure 1:
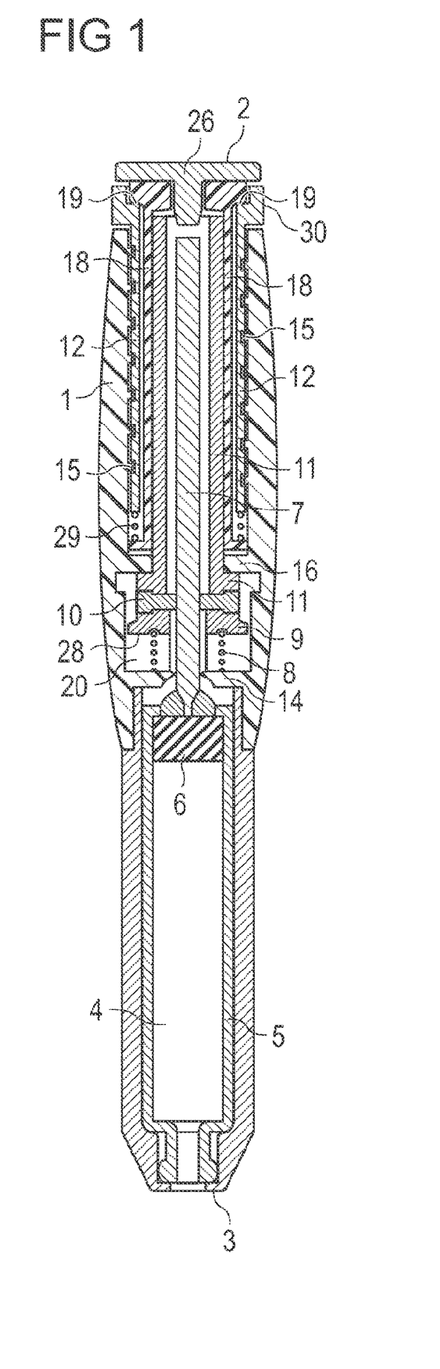
FIG. 1 shows a schematic cross-section of an injection pen comprising an embodiment of the drive mechanism.

FIG. 1 shows a schematic cross-section of an injection pen comprising an embodiment of the drive mechanism. The drug delivery device can have other suitable shapes instead. The device comprises a housing or body 1. The term "body" encompasses any exterior housing, like a main housing or shell, as well as an interior housing, like an insert or inner body arranged within an exterior housing. The body 1 can be composed of at least two attachable and separable parts enabling a refill of the device. In the embodiment shown in FIG. 1, the body 1 is of elongated shape. It has a proximal end 2 and a distal end 3. The distal end 3 can be provided with a needle, not shown in FIG. 1, or with a needle unit, for instance. The device may instead be needle-free. The drive mechanism may be operated by a dose button 26 at the proximal end 2. The device may be disposable or reusable, and it may be configured to dispense fixed doses of the drug or variable doses.

The body 1 comprises a receptacle 4 provided for a drug. The drug can be a liquid, especially insulin, heparin or growth hormones, for example. The term drug, as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39), des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Trp(O2)25] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(02)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The receptacle 4 can be designed to be filled by means of a cartridge 5 containing the drug and being inserted in the receptacle 4. A full cartridge 5 preferably contains a plurality of doses of the drug. When the cartridge 5 is empty, it can be removed and substituted with a new cartridge. The drug is dispensed through an opening of the receptacle by means of a piston 6, which is advanced in the receptacle 4, particularly within the cartridge 5, towards the distal end 3 by means of a piston rod 7. If the piston rod 7 is to be moved relatively to the piston 6, a bearing, schematically indicated in FIG. 1, can be arranged between the piston 6 and the piston rod 7 to reduce damages that may be caused by friction.

The piston rod 7 is arranged in the drive mechanism, which is placed in the body 1, preferably near the proximal end 2. The piston rod 7 is partially surrounded by a drive sleeve 11, a clutch sleeve 18, and a dose member 12. The dose member 12 is cylindrical and provided with a screw thread 15, which engages a corresponding thread in the inner surface of the body 1. The dose member 12 has a grip 30 outside the body 1 to enable the user to turn the dose member 12. When the dose member 12 is rotated, the thread 15 generates a helical movement of the dose member 12 with respect to the body 1. For the following, a first sense of rotation and a second sense of rotation with respect to the body 1 are defined by the specification that the helical movement of the dose member 12 with respect to the body 1 comprises a rotation having the first sense of rotation when the dose member 12 is moved in the proximal direction and a rotation having the second sense of rotation when the dose member 12 is moved in the distal direction.

The dose member 12 is coupled to the clutch sleeve 18 in a releasable manner by a clutch 19. The clutch 19 can be provided near the proximal ends of the clutch sleeve 18 and the dose member 12. The clutch 19 can be formed by a surface area of the clutch sleeve 18 and a corresponding surface area of the dose member 12, the surface areas touching each other and rotationally coupling the clutch sleeve 18 and the dose member 12 by means of friction. Instead, the clutch 19 can be formed by a structured surface area of the clutch sleeve 18, which may be an annular surface area provided with ratchet teeth, for instance, and a corresponding structured surface area of the dose member 12. When the clutch 19 is engaged, the clutch sleeve 18 and the dose member 12 are rotationally locked to one another. A spring 29 can be provided to hold the clutch 19 engaged when no force is exerted on the dose member 12.

The clutch sleeve 18 is rotationally locked to the drive sleeve 11 in such a manner that the clutch sleeve 18 can be shifted relatively to the drive sleeve 11 in the axial direction with respect to the body 1. This may be achieved by a groove or track guiding the relative movement of the clutch sleeve 18 and the drive sleeve 11. The drive sleeve 11 can be rotated with respect to the body 1, but a movement of the drive sleeve 11 in the distal direction or in the proximal direction is inhibited or at least restricted. To this purpose, the body 1 can be provided with stop means, which can be interfaces or webs 14, 16, for instance, which stop a shift of the drive sleeve 11 in the distal direction and in the proximal direction.

The embodiment according to FIG. 1 further comprises a spring 8, a stop member 9, and a drive member 10. These components of the drive mechanism couple the piston rod 7 with the drive sleeve 11 and can be substituted in other embodiments with other means to couple the piston rod 7 with the drive sleeve 11. The stop member 9 and the drive member 10 are rotationally coupled by a first gear, which is preferably a unidirectional gear and may be a ratchet. The drive member 10 and the drive sleeve 11 are rotationally coupled by a second gear, which is preferably also a unidirectional gear and may be a ratchet. While not meaning to restrict the scope of this designation, the word "ratchet" will be used in the following to denote a unidirectional gear that can be used in the drive mechanism. The stop member 9 is rotationally locked to the body 1, but is allowed to perform a reciprocating motion enabling the ratchets to engage and disengage during a rotation in the permitted direction. The stop member 9, the drive member 10, and the drive sleeve 11 are held in contact by the action of the spring 8, which is supported by the web 14 of the body 1.

The ratchets allow unidirectional rotations of the drive member 10 with respect to the stop member 9 and with respect to the drive sleeve 11. In both of these relative movements, the drive member 10 rotates in the same sense of rotation with respect to the proximal direction. This means that, depending on the sense of rotation of the drive sleeve 11 with respect to the body 1, either the drive sleeve 11 is rotationally locked to the drive member 10, which rotates together with the drive sleeve 11 relatively to the body 1 and to the stop member 9, or the drive sleeve 11 rotates relatively to the body 1 and to the drive member 10, which is rotationally locked to the stop member 9. According to the above definition, the drive member 10 is rotationally locked to the stop member 9 when the drive sleeve 11 is rotated in the first sense of rotation with respect to the body 1, and the drive member 10 is rotationally locked to the drive sleeve 11 when the drive sleeve 11 is rotated in the second sense of rotation with respect to the body 1.

The drive member 10 essentially stays at its position within the body 1 and is rotationally locked to the piston rod 7, while the piston rod 7 is able to move axially with respect to the body 1 in the distal direction or in the proximal direction. Because the movement of the piston rod 7 is guided with respect to the body 1, as will be described in conjunction with FIG. 6, a rotation of the piston rod 7 by means of the drive member 10 generates a helical movement of the piston rod 7 relatively to the body 1. A rotation of the drive member 10 that is permitted by the stop member 9 is thus converted into a helical movement of the piston rod 7 shifting the piston rod 7 in the distal direction.

When the dose member 12 is helically moved in the proximal direction according to the thread 15, in the first sense of rotation with respect to the body 1, the clutch sleeve 18 and the dose member 12 are rotationally locked by the engaged clutch 19. As the clutch sleeve 18 is rotationally locked to the drive sleeve 11, the drive sleeve 11 also rotates in the first sense of rotation. Therefore the drive member 10 is rotationally locked to the stop member 9, and the rotation of the drive sleeve 11 overrides the ratchet coupling the drive sleeve 11 and the drive member 10. Consequently, the piston rod 7 does not rotate.

Figure 2:
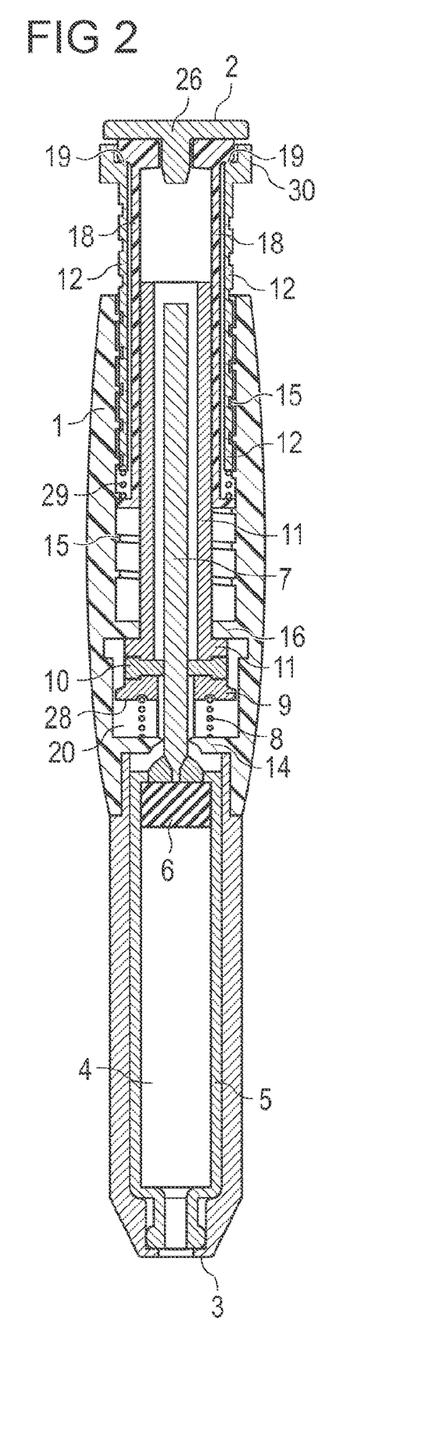
FIG. 2 shows a cross-section according to FIG. 1 after the setting of a dose.

FIG. 2 shows a cross-section of the drive mechanism according to FIG. 1 after the setting of a dose. Further to the grip 30, a portion of the dose member 12 now juts out of the body 1. The clutch sleeve 18 was moved together with the dose member 12, and the clutch 19 is still engaged. A correction of the set dose is easily possible by moving the dose member 12 with respect to the body 1 back in the distal direction, in the second sense of rotation, the movement being again helical and guided by the thread 15. This can be achieved by turning the grip 30 in the opposite direction. A slight pressure exerted on the dose member 12 in the distal direction against the action of the spring 29 causes the clutch 19 to disengage, so that the dose member 12 is rotated while the clutch sleeve 18 is only axially moved without rotating relatively to the body 1. To make the clutch 19 disengage when the dose member 12 is moved in the distal direction, it may be favorable if the movement of the clutch sleeve 18 is retarded by friction. This may be achieved by protruding parts of the clutch sleeve 18, like the rims supporting the spring 29, for instance, sliding on the inner wall of the body 1. Consequently, the drive member 11 does not rotate during the correcting set operation, and the piston rod 7 is not moved. The dose member 12 is thus moved until the desired position of the dose member 12 is obtained. The correct value of the set dose may be indicated by a scale or a numbering applied to the dose member 12. Audible and/or tactile means can also be provided to guide the user when setting a dose.

A selected dose is delivered by pressing the dose button 26 in the distal direction. The dose button 26 acts on the clutch sleeve 18, which is arranged in such a manner that a shift of the clutch sleeve 18 in the distal direction simultaneously shifts the dose member 12. The clutch 19 stays engaged, and the clutch sleeve 18 follows the helical movement of the dose member 12 with respect to the body 1. The dose button 26 is preferably rotatable relatively to the clutch sleeve 18, so that the rotation of the clutch sleeve 18 is possible without a rotation of the dose button 26. The clutch sleeve 18, which is rotationally locked to the drive sleeve 11, generates a rotation of the drive sleeve 11 in the second sense of rotation, which is transferred to the drive member 10 and thus to the piston rod 7. The piston rod 7 advances helically towards the distal end 3 and shifts the piston 6 until the selected dose is expelled.

Figure 3:
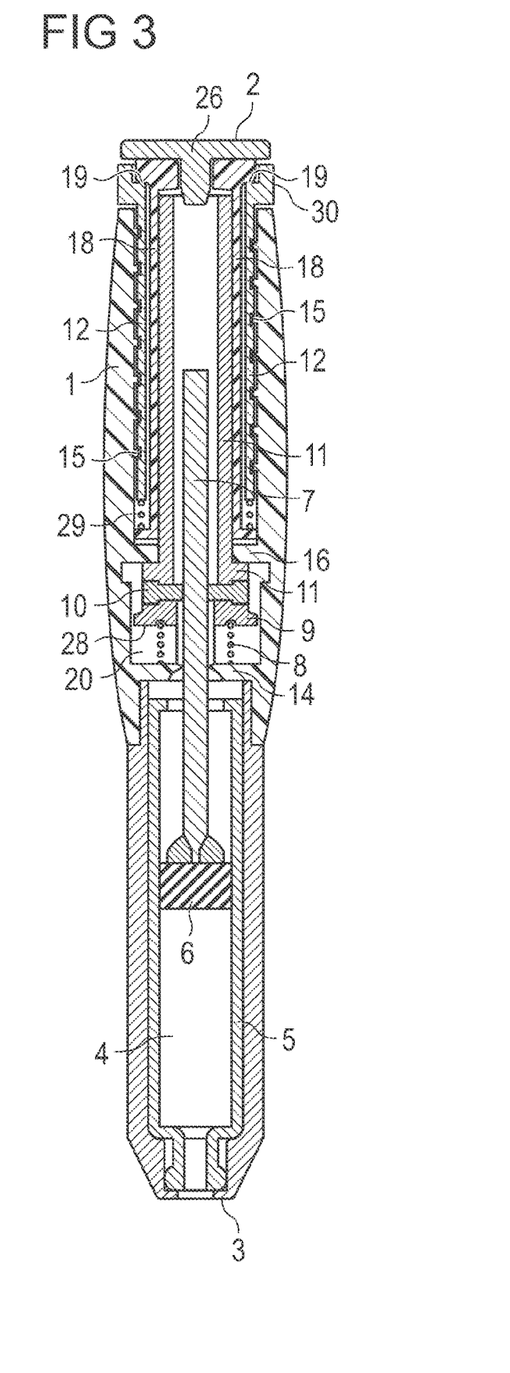
FIG. 3 shows a cross-section according to FIG. 1 after the delivery of several doses.

FIG. 3 shows a cross-section of the drive mechanism after the delivery of several doses. The dose member 12 is again in the position which it occupied when the device was in the initial state shown in FIG. 1. The position of the piston rod 7 is now changed, because the piston rod 7 was shifted several times in the distal direction in the course of delivery operations. The other components of the drive mechanism are arranged according to the state shown in FIG. 1, and a further set operation can be performed by turning the dose member 12.

Whereas the dose member 12 is rotated in the first sense of rotation during the setting of the dose, the rotation of the drive sleeve 11 during the delivery operation takes place in the second sense of rotation with respect to the body 1, and the drive member 10 as well as the piston rod 7 are rotated. During a correcting set operation, the clutch 19 is disengaged to avoid a rotation of the drive sleeve 11 in the second sense of rotation. The piston rod 7 is moved only in delivery operations, when the clutch 19 is held engaged by pressing the dose button in the distal direction.

Figure 4:
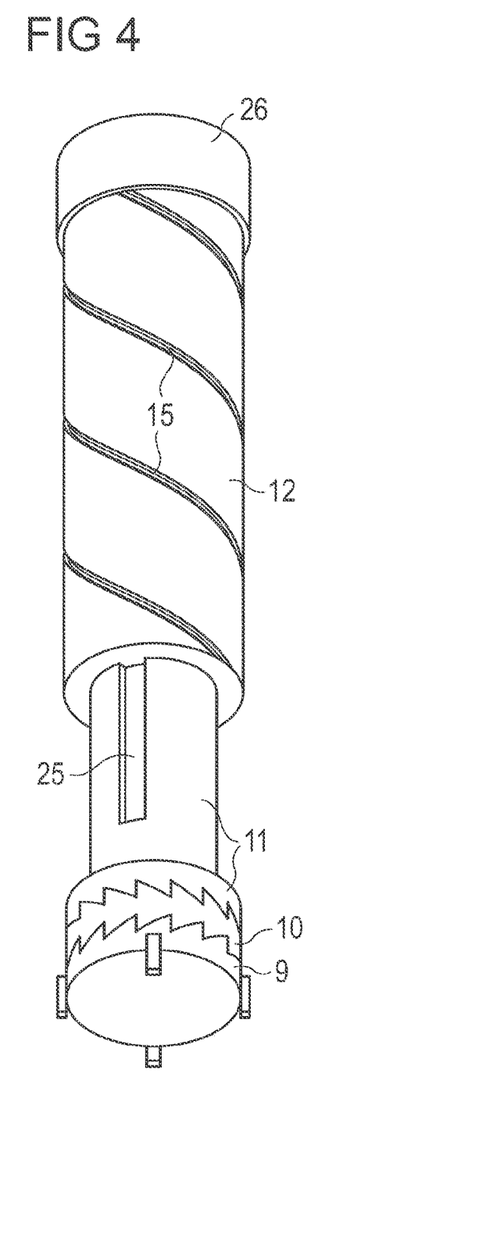
FIG. 4 shows a perspective view of a part of a drive mechanism.

FIG. 4 shows a perspective view of a part of an embodiment of the drive mechanism. The stop member 9, the drive member 10 and the drive sleeve 11 are engaged by a ratchet coupling the drive member 10 and the stop member 9 and by a ratchet coupling the drive member 10 and the drive sleeve 11. The ratchets and their function will be described in more detail below. The drive sleeve 11 is arranged within a dose member 12, which is provided with a screw thread 15. The drive sleeve 11 and the dose member 12 are rotationally locked, which may be achieved by an axial groove 25 of the drive sleeve 11, for example. The drive sleeve 11 can be moved axially with respect to the dose member 12, but not rotated with respect to the dose member 12. The dose member 12 is provided with the dose button 26. In the embodiment according to FIG. 4, there is no clutch sleeve 18, and the dose member 12 is directly engaged with the drive sleeve 11.

Moving the dose member 12 in the proximal direction sets a dose which is to be delivered and moving the dose member 12 in the distal direction effects a delivery of the set dose. The dose member 12 is guided by the screw thread 15 on a helical movement with respect to the body 1. Proximal and distal end positions of the movement of the dose member 12 may be determined by respective stop features provided at the body 1.

Figure 5:
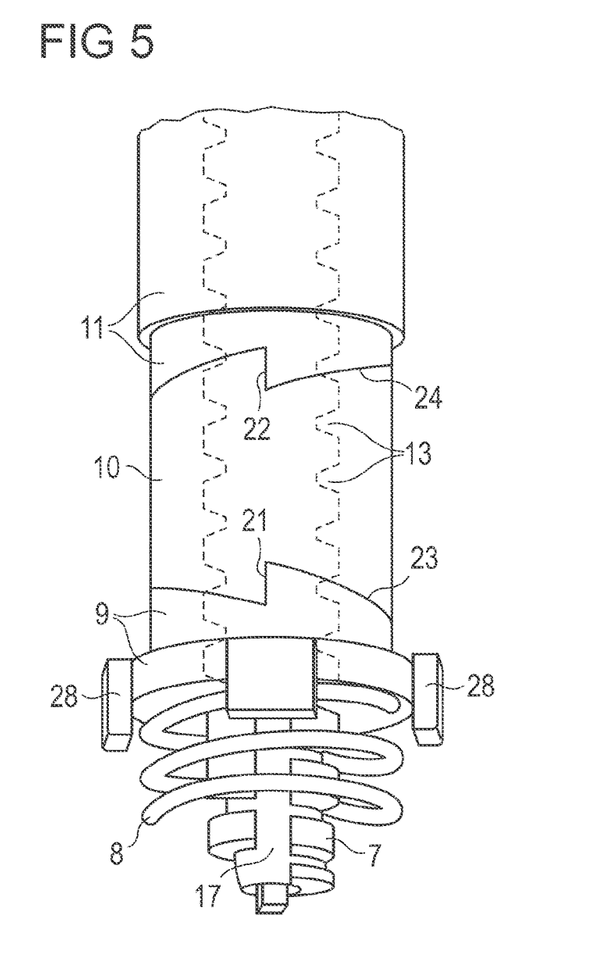
FIG. 5 shows a detailed view of a part of an embodiment of the drive mechanism comprising a stop member, a drive member, and a drive sleeve.

FIG. 5 shows the unidirectional gears between the stop member 9, the drive member 10 and the drive sleeve 11. The drive sleeve 11 is coupled to the drive member 10 by a ratchet, which permits a rotation of the drive sleeve 11 with respect to the drive member 10 when the drive sleeve 11 rotates in the first sense of rotation with respect to the body 1. The ratchet prevents a rotation of the drive sleeve 11 relatively to the drive member 10, when the drive sleeve 11 rotates in the second sense of rotation with respect to the body 1. The drive member 10 thus follows a rotation of the drive sleeve 11 in the second sense of rotation during a delivery operation.

The drive member 10 comprises teeth being disposed azimuthally along the perimeter of the components and forming a first gear 21 coupling the drive member 10 and the stop member 9 and a second gear 22 coupling the drive member 10 and the drive sleeve 11. Ramps 23 of the first gear 21 and ramps 24 of the second gear 22 are arranged in such a fashion that a relative rotation of two components that are directly coupled by one of the gears is possible in one sense of rotation while the relative rotation of those two components is inhibited in the opposite sense of rotation. Thus the rotational coupling described above is achieved. The stop member 9 can be provided with protruding parts like the teeth 28 shown in FIG. 5 to allow a rotational locking of the stop member 9 with the body 1. If the teeth 28 are guided in axial grooves in the body 1, the stop member 9 can be moved axially, but not rotated with respect to the body 1. This clearly shows that a rotation of the drive sleeve 11 in the first sense of rotation takes place without rotation of the drive member 10, because the drive member 10 is engaged with the rotationally fixed stop member 9, and a rotation of the drive sleeve 11 in the second sense of rotation makes the drive member 10 rotate simultaneously and relatively to the stop member 9. During the setting of a dose the drive member 10 does not rotate, and during a delivery of a dose the drive member 10 rotates to generate a simultaneous rotation of the piston rod 7 according to the further mechanism that will now be described in conjunction with FIGS. 6 and 7.

Figure 6:
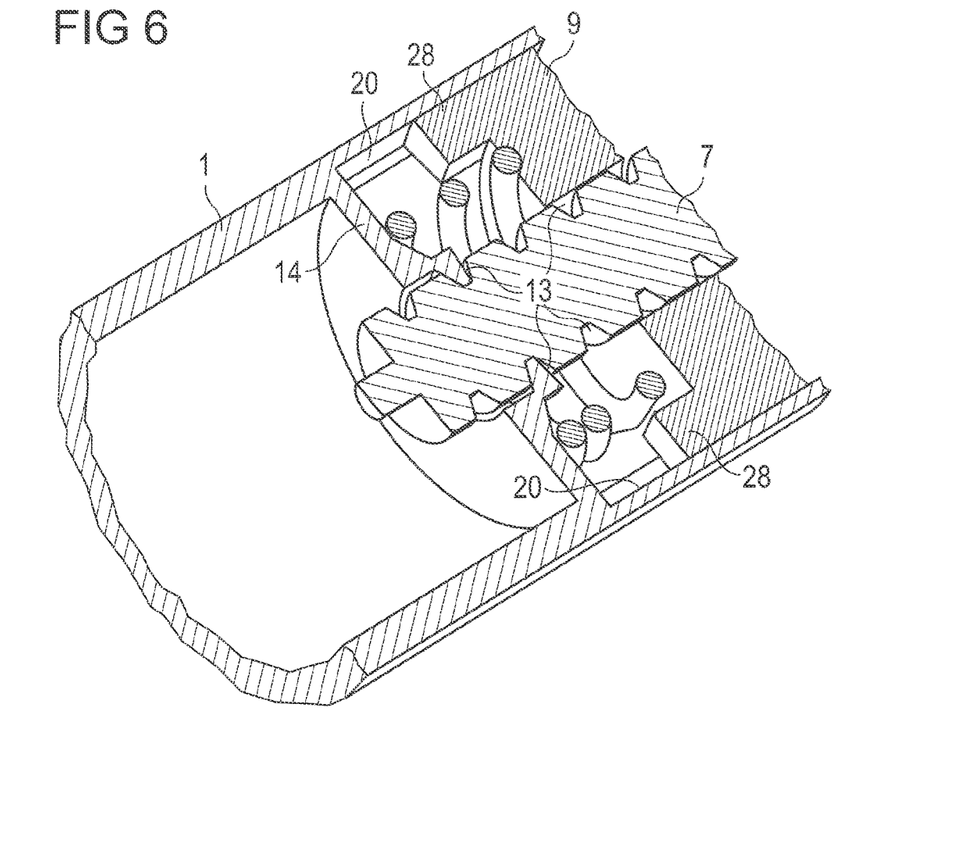
FIG. 6 shows a cross-section of a part of an embodiment of the drive mechanism comprising a body, a piston rod, and a means guiding the piston rod in a helical movement.

FIG. 6 shows a cross-section of a part of an embodiment of the drive mechanism having means for guiding the piston rod 7 in a helical movement with respect to the body 1. The drive mechanism comprises a spring 8, which is provided to hold the stop member 9 in contact with the drive member 10. FIG. 6 shows a possible arrangement of the spring 8 being supported by an internal interface or web 14 of the body 1. The web 14 has an opening with a guide means guiding the movement of the piston rod 7. To this end, the piston rod 7 is provided with a screw thread 13, which generates a helical movement of the piston rod 7 with respect to the body 1, when the piston rod 7 is moved through the opening of the web 14.

The stop member 9 is shown to have teeth 28, which are guided within axial guides 20 formed in an inner surface of the body 1. This is an example of a rotational coupling between the stop member 9 and the body 1, which enables an axial relative movement.

If the stop member 9 is shifted in the distal direction, the spring 8 is compressed. The spring force drives the stop member 9 in the proximal direction, so that the stop member 9 is held in contact with the adjacent drive member 10, which stays in contact with the drive sleeve 11. The spring 8 thus allows for a small axial movement of the stop member 9 and the drive member 10 relatively to the drive sleeve 11 to facilitate relative rotations involving a sliding motion over the ramps 23, 24.

Figure 7:
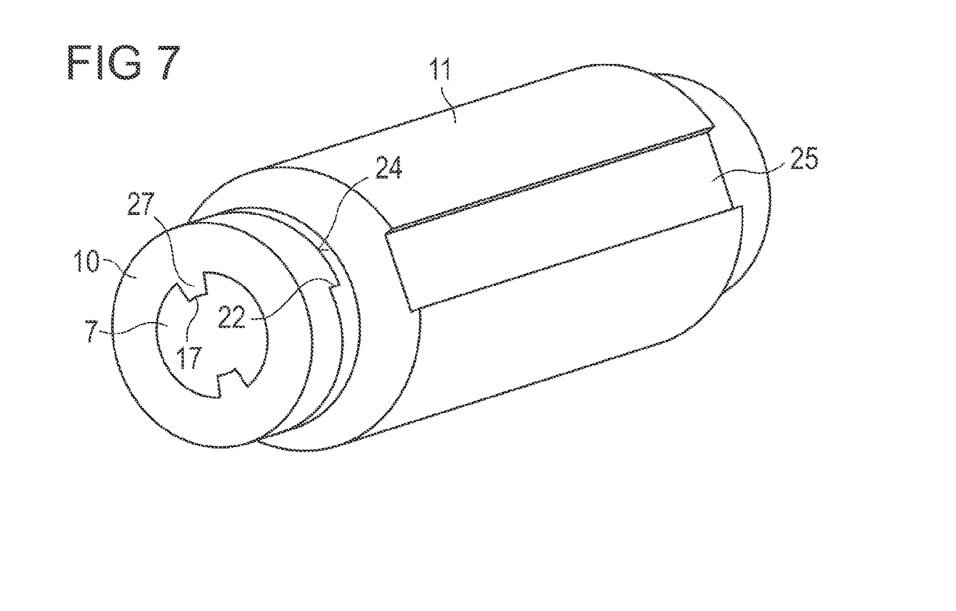
FIG. 7 shows a perspective view of a part of an embodiment of the drive mechanism comprising a dose sleeve, a drive sleeve, a drive member, and a piston rod.

FIG. 7 shows how the piston rod 7 may be rotationally coupled to the drive member 10. To this purpose, the piston rod 7 comprises at least one axial groove 17 or engagement track cutting the screw thread of the piston rod 7 in the axial direction, as can be seen from FIG. 5. An axial thread 27 of the drive member 10 engages the axial groove 17 of the piston rod 7 and thus allows a relative axial movement of the piston rod 7 with respect to the drive member 10 while at the same time coupling the drive member 10 and the piston rod 7 rotationally. FIG. 7 also shows the second gear 22 coupling the drive member 10 and the drive sleeve 11. In this embodiment, the drive sleeve 11 is provided with the axial groove 25 also shown in FIG. 4.

Although the present invention and its advantages have been described in detail, it should be understood that various changes, substitutions and alterations can be made herein without departing from the spirit and scope of the invention as defined by the appended claims.

The invention claimed is:

1. A drive mechanism for a drug delivery device, comprising:
    a body having a proximal end and a distal end,
    a piston rod arranged within the body along an axis of rotation,
    a dose member having a thread, the thread engaging a corresponding thread of the body to allow a helical movement of the dose member with respect to the body, the helical movement comprising a rotation around the axis and a simultaneous shift along the axis,
    a drive sleeve arranged within the body, rotatable with respect to the body around the axis and rotationally coupled to the dose member,
    a proximal stop interface provided to restrict a movement of the drive sleeve in the proximal direction with respect to the body,
    a distal stop interface provided to restrict a movement of the drive sleeve in the distal direction with respect to the body,
    a stop member arranged within the body and being rotationally locked to the body with respect to the axis and being axially movable with respect to the body along the axis,
    a drive member arranged within the body, the drive member being rotationally locked to the piston rod and held in contact with the stop member,
    a first gear locking the drive member unidirectionally rotationally to the stop member in a first sense of rotation with respect to the body, and
    a second gear locking the drive member rotationally to the drive sleeve when the drive sleeve is rotated in a second sense of rotation, which is opposite to the first sense of rotation, with respect to the body.

2. The drive mechanism according to claim 1, wherein the thread of the dose member is arranged in such a manner that the helical movement of the dose member with respect to the body comprises a rotation having the first sense of rotation when the dose member is moved towards the proximal end and a rotation having the second sense of rotation when the dose member is moved towards the distal end.

3. The drive mechanism according to claim 1, wherein the piston rod has a thread guiding the piston rod in the body in such a manner that the piston rod advances towards the distal end when the piston rod is rotated in the second sense of rotation with respect to the body.

4. The drive mechanism according to claim 1, wherein the drive sleeve is rotationally locked to the dose member.

5. The drive mechanism according to claim 1, further comprising:
    a clutch sleeve arranged between the dose member and the drive sleeve,
    the clutch sleeve forming a clutch, which couples the clutch sleeve rotationally with the dose member in a releasable manner,
    the clutch sleeve being rotationally locked to the drive sleeve.

6. The drive mechanism according to claim 5, wherein the clutch locks the clutch sleeve unidirectionally rotationally to the dose member.

7. The drive mechanism according to claim 6, wherein the unidirectional rotational locking of the clutch sleeve with the dose member generates a rotation of the clutch sleeve during a helical movement of the dose member with respect to the body in the proximal direction.

8. The drive mechanism according to claim 5, further comprising: a resilient element acting on the clutch sleeve and the dose member so that the clutch sleeve and the dose member are rotationally locked to one another when the clutch is engaged, the resilient element being arranged in such a manner that moving the dose member in the distal direction reduces or removes the engagement of the clutch.

9. The drive mechanism according to claim 5, wherein the dose member can be moved helically in the distal direction without rotating the clutch sleeve.

10. The drive mechanism according to claim 1, wherein a set operation is performed by a helical movement of the dose member with respect to the body in the proximal direction, the helical movement being guided by the thread of the dose member.

11. The drive mechanism according to claim 1, wherein a dispense operation is performed by a helical movement of the dose member with respect to the body in the distal direction, the helical movement being guided by the thread of the dose member, and the drive sleeve rotating simultaneously.

12. The drive mechanism according to claim 1, wherein a correcting set operation is performed by a helical movement of the dose member with respect to the body in the distal direction, the helical movement being guided by the thread of the dose member, and the drive sleeve being stationary with respect to the body.

13. A drug delivery device, comprising of a drive mechanism according to claim 1.

14. The drug delivery device according to claim 13, wherein the body has a shape of an injection pen.

* * * * *